(12) United States Patent (10) Patent No.: US 9,161,906 B2
Mazzone et al. (45) Date of Patent: Oct. 20, 2015

(54) PHARMACEUTICAL FORMULATIONS BASED ON APOLAR AND POLAR LIPIDS FOR OPHTHALMIC USE

(75) Inventors: Maria Grazia Mazzone, Acireale (IT); Valeria Maria Carmela Moschetti, Gravina di Catania (IT); Fausto Giuseppe Miano, Tremestieri Etneo (IT); Letizia Gaetana Lo Grasso, Gravina di Catania (IT)

(73) Assignee: SIFI, S.P.A., Lavinaio-Aci Sant-Antonio (Catania) (IT)

( * ) Notice: Subject to any disclaimer, the term of this patent is extended or adjusted under 35 U.S.C. 154(b) by 832 days.

(21) Appl. No.: 12/593,075

(22) PCT Filed: Dec. 24, 2007

(86) PCT No.: PCT/EP2007/064530
§ 371 (c)(1),
(2), (4) Date: May 12, 2010

(87) PCT Pub. No.: WO2008/119401
PCT Pub. Date: Oct. 9, 2008

(65) Prior Publication Data
US 2010/0291226 A1 Nov. 18, 2010

(30) Foreign Application Priority Data
Mar. 30, 2007 (WO) .................... PCT/IT2007/00239

(51) Int. Cl.
A61K 9/48 (2006.01)
A61K 9/00 (2006.01)
A61K 47/24 (2006.01)
A61K 47/44 (2006.01)

(52) U.S. Cl.
CPC ............... *A61K 9/0048* (2013.01); *A61K 47/24* (2013.01); *A61K 47/44* (2013.01)

(58) Field of Classification Search
None
See application file for complete search history.

(56) References Cited

U.S. PATENT DOCUMENTS 5,578,586 A 11/1996 Glonek et al.
2005/0049209 A1* 3/2005 Chen ............................... 514/28
2006/0177430 A1* 8/2006 Bhushan et al. ............. 424/94.1
2006/0182771 A1 8/2006 Dor et al.
2007/0015710 A1 1/2007 Chang et al.
2007/0218007 A1 9/2007 Chang et al.

FOREIGN PATENT DOCUMENTS

| JP | 2000 143542 | 5/2000 |
| WO | 94/05298 | 3/1994 |
| WO | 02/09667 | 2/2002 |
| WO | 03/053405 | 7/2003 |
| WO | 2004/082625 | 9/2004 |

OTHER PUBLICATIONS

European Journal of pharmaceutics and Biopharmaceutics 58 (2004), (357-365). The potential of lipid emulsion for ocular delivery of lipophilic drugs, Shunmugaperumal Tamilvanan.*
Miano F. et al, J. Phys: Condens. Matter 16 (2004) S2461-S2467.
Bloch JK et al., "Potentiated reagin response: Initiation with minute doses of antigen and alum followed by infection with *Nippostrongylus brasiliensis*" J Immunol 110:197, 1973.
Caloenge MC et al., "Pharmacologic modulation of vascular permeability in ocular allergy in the rat". Invest Ophthalmol Vis Sci 28: 264, 1987.
Tamilvanan et al., "The potential of lipid emulsion for ocular delivery of lipophilic drugs", European Journal of Pharmaceutics and Biopharmaceutics 58, 2004, pp. 357-368, Elsevier B.V.
Zurowska-Pryczkowska et al., "Studies on the effect of pilocarpine incorportion into a submicron emulsion on the stability of the drug and the vehicle", European Journal of Pharmaceutics and Biopharmaceutics 47, 1999, pp. 255-260, Elsevier Science B.V.
Baird et al, "Edema test for assessing ocular anaphylaxis", Current Eye Research, vol. 2, No. 10, 1982/1983, pp. 657-661, IRL Press Limited, Oxford, England.
Calvo et al., "Improved Ocular Bioavailability of Indomethacin by Novel Ocular Drug Carriers", J. Pharm. Pharmacol. 48, 1996, pp. 1147-1152, Spain.

* cited by examiner

*Primary Examiner* — Snigdha Maewall
(74) *Attorney, Agent, or Firm* — Davis & Bujold, P.L.L.C.; Michael J. Bujold (57) ABSTRACT

The present invention refers to pharmaceutical formulations based on lipids for ophthalmic use comprising a phospholipid component composed of zwitterionic phospholipids of natural origin and an oily component composed of oils of natural origin emulsified in water. In particular, the invention refers to ophthalmic formulations useful, for example, for transporting drugs to the eye and in the treatment of ocular dryness, capable of restoring the lipid layer of the tear film. In particular, in a non-transitory but pathological situation such as the dry eye syndrome, such formulations also succeed in reducing the often-present inflammatory component.

28 Claims, 6 Drawing Sheets

| Oil | Soy | Sesame | Corn | Cotton | Olive | Fish | Mineral |
|---|---|---|---|---|---|---|---|
| Myristic 14:0 | | | | 0.3 | | | |
| Palmitic 16:0 | 9-13 | 9.1 | <1 | 19.1 | | | |
| Stearic 18:0 | 3-6 | 4.3 | <1.7 | 1.9 | | | |
| Oleic 18:1 | 17-26 | 45.4 | <25.8 | 33.1 | >73.3 | | |
| Linoleic 18:2 | 50-57 | 40.4 | >39.9 | 39.3 | >8.2 | | |
| Linolenic 18:3 | 5-10 | | 1.1 | | <1 | | |
| Arachidonic 20:0 | | 0.9 | | 0.6 | | | |
| Eicosapentaenoic 20:5 | | | | | | >13 | |
| Docosenoic 22:6 | | | | | | >9 | |
| Palmitoleic 16:1 | | | | | 1 | | |
| Other | | | ethers, glycosides | phospholipids, phytosterols, pigments | ω-3 total >20 | saturated | |
| Pharmacopoeia JP, PhEur, USP | JP, EurPh, USP | | JP, EurPh, USP | JP, EurPh, USP | | EurPh | USP |

PHARMACEUTICAL FORMULATIONS BASED ON APOLAR AND POLAR LIPIDS FOR OPHTHALMIC USE

FIELD OF THE INVENTION

The present invention refers to lipid-based pharmaceutical formulations for ophthalmic use. In particular, the invention refers to ophthalmic formulations which are useful, for example, for transporting drugs to the eye and in the treatment of ocular dryness, since they are capable of restoring the lipid layer of the tear film. In particular, in a non-transitory but pathological situation such as the dry eye syndrome, such formulations also succeed in reducing the often-present inflammatory component.

BACKGROUND OF THE INVENTION

It is known that the function of the tear film is that of keeping the ocular surface wet, protecting the corneal and conjunctival epithelium and transporting biologically active substances which are useful for the physiology of the eye (nutrients, oxygen). To preserve the physical characteristics of the ocular epithelium, the tear film must have a proper surface tension (proper capacity of the mucous layer to permits the aqueous phase to be extended on the epithelium) and must have a physiological evaporation speed. The alteration of these properties determines the rise of ocular dryness and possibly dry eye syndrome.

The tear film is substantially composed of three layers. The first adheres to the ocular surface (cornea, conjunctiva) and is mainly composed of mucin; the intermediate layer is substantially composed of an aqueous solution containing ions, proteins etc.; the third layer, in contact with the air, is mainly composed of non-polar and polar lipids of different nature (cholesterol, cholesterol esters, phospholipid triglycerides, ceramides, cerebrosides etc.) having the function of avoiding a sudden evaporation of the intermediate aqueous layer.

In reality, such layers are in dynamic equilibrium with each other, due to the eyelid blinking, which causes an overall more complex and homogenous tear film.

One cause of the onset of ocular dryness and in particular of dry eye is the excessive evaporation of the aqueous layer of the tear film caused by a poor functionality of the outer lipid layer following qualitative-quantitative modifications of its composition.

Ophthalmic compositions are on the market containing polymers which reduce the evaporation of the tear film due to a certain viscosity level.

Other compositions based on phospholipids or oil emulsions in water are used in order to restore the natural lipid layer of the tear film, always with the function of reducing the evaporation of the aqueous film. These compositions are for instance reported in the Glonek patent, U.S. Pat. No. 5,578,586.

In particular, the aforesaid patent describes a specific and metastable formulation, composed of a phospholipid component and an oily component, at determined concentrations and ratios thereof emulsified in water.

In the indicated patent, the phospholipid component is composed of charged phospholipids (net positive or negative charge) in quantities in the range of 0.01%-7% by weight on the total weight of the composition, while the oily component is composed of mineral oils in quantities between 0.1%-12.5% by weight on the total weight of the composition.

The patent specifies, in particular, that this oil type, defined "non-polar", is preferred to that of animal or vegetal origin, defined "polar" (since they contain a significant number of acid and/or ester groups), since the latter would cause undesired effects of sight dimming and composition instability with respect to synthetic oils.

It should be noted that, with regard to the phospholipids, zwitterionic molecules such as phosphatidylethanolamine and phosphatidylcholine (lecithin) are explicitly excluded from the scope of U.S. Pat. No. 5,578,586, since they are provided with a positive charge which, at pH 7, cancels the negative charge of the phosphate group. Negatively-charged phospholipids are preferred according to this patent, as the negative charge which they impart would facilitate, by a light electrostatic repulsion with the ocular surface negatively-charged, the extension of the composition on the ocular surface.

Moreover, all formulations containing lipids which are available on the market today require being preserved at low temperature (4° C.) due to the poor stability of the lipid component which grows rancid at room temperature.

SUMMARY OF THE INVENTION

The technical problem underlying the present invention is therefore that of finding pharmaceutical compositions for ophthalmic use which are different from the known compositions, and which are stable and well-tolerated and in addition useful as a vehicle for active principles. In particular, the compositions of the invention are provided with optimal effectiveness in the treatment of ocular dryness and/or dry eye, even of small size.

Such problem is resolved by pharmaceutical compositions comprising a selection of particular lipids (phospholipids and oils) of natural origin. In fact, it was surprisingly found that the use of non-polar lipids, in particular of vegetal or animal origin (for example soy oil, olive oil, fish oil) and polar lipids, such as the phospholipids deriving from egg yolk or soy lecithin or a mixture of phospholipids such as phosphatidylcholine, phosphatidylethanolamine, sphingomyelin, permits reducing the evaporation of the aqueous part of the tear film in a manner similar to the Meibomian gland (natural lipid layer of the tear), as well as reducing such evaporation in a more effective manner than the formulations, emulsified or containing polymers, currently present on the market.

As will be seen by the examples, the compositions of the invention succeed better than others in effectively reducing the evaporation of the tear film. Moreover, the other tested formulations, the products found on the market, could not be integrated with the natural Meibomian gland, as were on the other hand compositions described below.

In addition, it was surprisingly observed that several compositions of the invention are effective for combating inflammatory or allergic conditions at the ocular level, correlated or not to the dry eye condition.

The compositions can moreover be used as a vehicle for active principles for ocular pathologies (glaucoma, Age-Related Macular Degeneration AMD, diabetic retinopathy, neuropathies, bacterial or viral infections, etc. . . . ) and in particular for substances with anti-allergic and/or anti-inflammatory activity, also not connected with dry eye, which could be assisted by the intrinsic effectiveness of the emulsions.

It is to be noticed that the pharmaceutical composition can be advantageously used as carrier for active principles thanks to its improved structure and capacity to carry said principles, as active principle per se due to the above identified therapeutic effect and/or as active principle showing an either additive or synergistic effect with active principles with anti-inflammatory or anti-allergic activity.

A first object of the invention is therefore that of making available pharmaceutical compositions for ophthalmic use as stated in the main attached claim.

A second object is that of ensuring the stability of said formulations even at room temperature.

A third object is that of making available a process for the production of said pharmaceutical compositions.

A fourth object is the use of said compositions for the production of a medication for the treatment of ocular pathologies such as, for example, glaucoma, Age-Related Macular Degeneration AMD, diabetic retinopathy, neuropathies, bacterial or viral infections, ocular dryness and dry eye.

A fifth object is the use of said compositions for the treatment of inflammatory conditions connected with, or not connected with, dry eye syndromes or ocular allergy conditions.

A sixth object consists of the use of the compositions as active principle vehicles for ophthalmic use and in particular for those whose effectiveness can be assisted by the pharmacological activity characterising the claimed compositions (anti-allergic, anti-inflammatory).

BRIEF DESCRIPTION OF THE FIGURES

Further characteristics and advantages of the present invention will be more evident from the following description of several embodiments given as non-limiting examples with reference to the figures, wherein, with regard to the stability of the claimed compositions:

DETAILED DESCRIPTION OF THE INVENTION

The ophthalmic compositions of the invention comprise a phospholipids component composed of zwitterionic phospholipids of natural origin and an oily component composed of oils of natural origin emulsified in water.

That which was surprisingly observed during the development of the compositions, object of the present invention, is that it was not the electric charge of the composition (conferred by the contained phospholipids) to cause its capacity to extend on the ocular surface in an efficient and effective manner for the reduction of the tear film evaporation, but the particular composition of the oily phase, in terms of identity and preferably percentages both of phospholipids and oils and their reciprocal ratios.

The ratio between the oily component and the phospholipids component can vary from 4:1-1:1, preferably it is 3:1, still more preferably the ratio is about 2.3:1.

In general, the phospholipids are present in the ophthalmic composition in quantities which vary from 0.01%-7% by weight on the total weight of the composition, preferably they vary from 0.1%-5%, still more preferably between 0.3%-3%.

In particular, the phospholipid component comprises zwitterionic phospholipids of natural origin such as mostly phosphatidylcholine in quantities from 50-70% and others in lower quantities including phosphatidylethanolamine from 5-20%, sphingomyelin from 1-10%, lysophosphatidylcholine from 1-10%, neutral lipids from 2%-15% etc. with respect to the phospholipid total. For example, one phospholipid component which comprises the aforesaid phospholipids is available with the commercial name of Egg Phospholipid 90 of the company Fresenius Kabi.

Advantageously, to further increase the stability and effectiveness of the claimed compositions, the esters of fatty acids present in the phospholipid fatty part are preferably chosen among in the quantities of: myristic acid ≤1%, palmitic acid 20-40%, palmitoleic acid ≤5%, stearic acid ≤30%, oleic acid 20-40%, linoleic acid (LA) ≤30%, eicosenoic acid ≤10%, arachidonic acid (AA) ≤5%, docosahexaenoic acid (DHA) ≤20% and other fatty acids of the Omega-3 series.

Among these, the fatty acids containing double bonds stabilise the emulsion, carrying out an antioxidant action.

The oily component comprises oils of essentially natural origin, such as for example soy oil, olive oil, sunflower oil, fish oil, borage oil, sesame oil, hemp oil, corn oil, cotton oil. It should be understood that the oily component must only comprise natural oils in the form of apolar triglycerides with the exclusion of synthetic oils and oils of mineral origin.

With the term apolar triglycerides in the present description it is intended lipid macromolecules consisting of a glycerol molecule whose hydroxylic groups (—OH) are esterified with three fatty acids, which can be the same or different from each other.

The triglycerides are present in the composition, object of the invention, in quantities which vary from 0.01%-28% by weight on the total weight of the composition, preferably from 0.3%-15%, still more preferably between 0.7%-7%.

Figure 2:
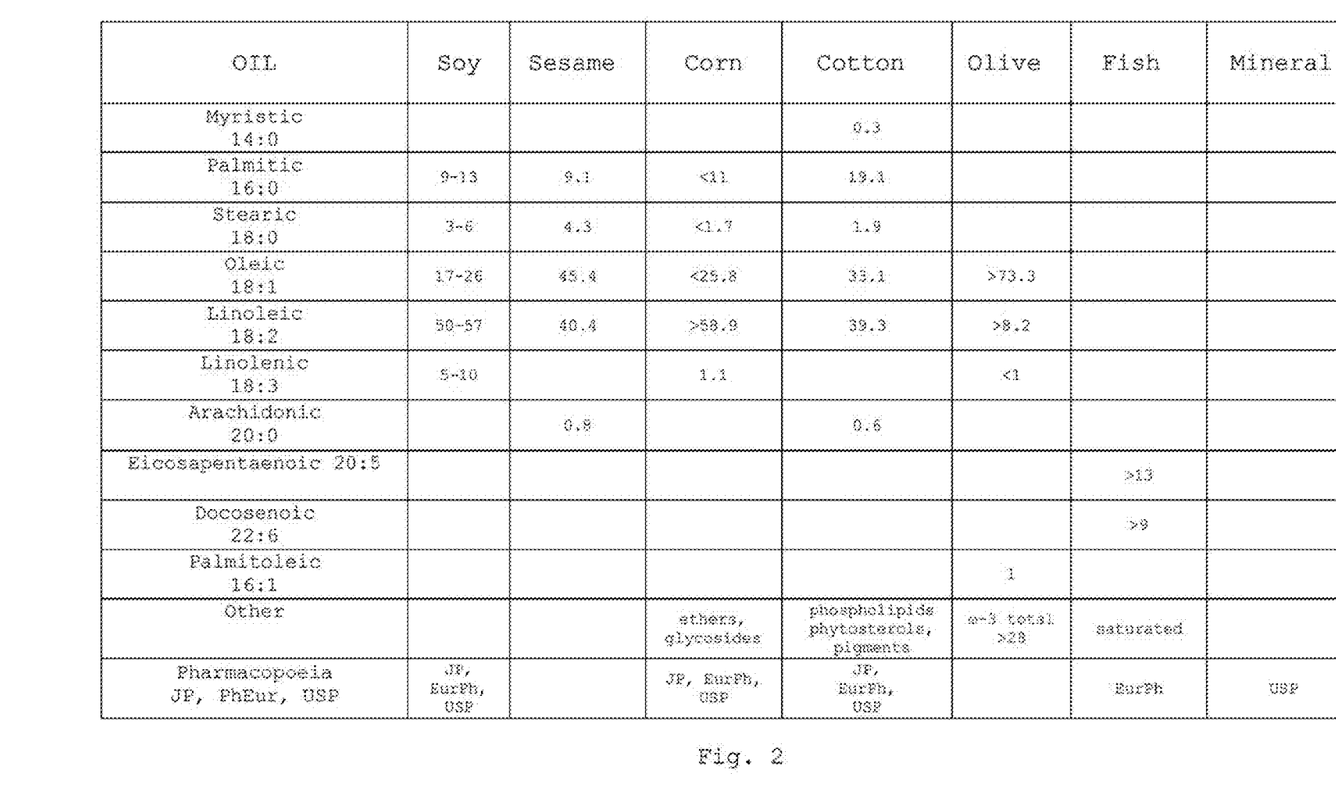
FIG. 2 represents a table with the composition percentage of the fatty acid esters in triglycerides of different origin.
Figure 3:
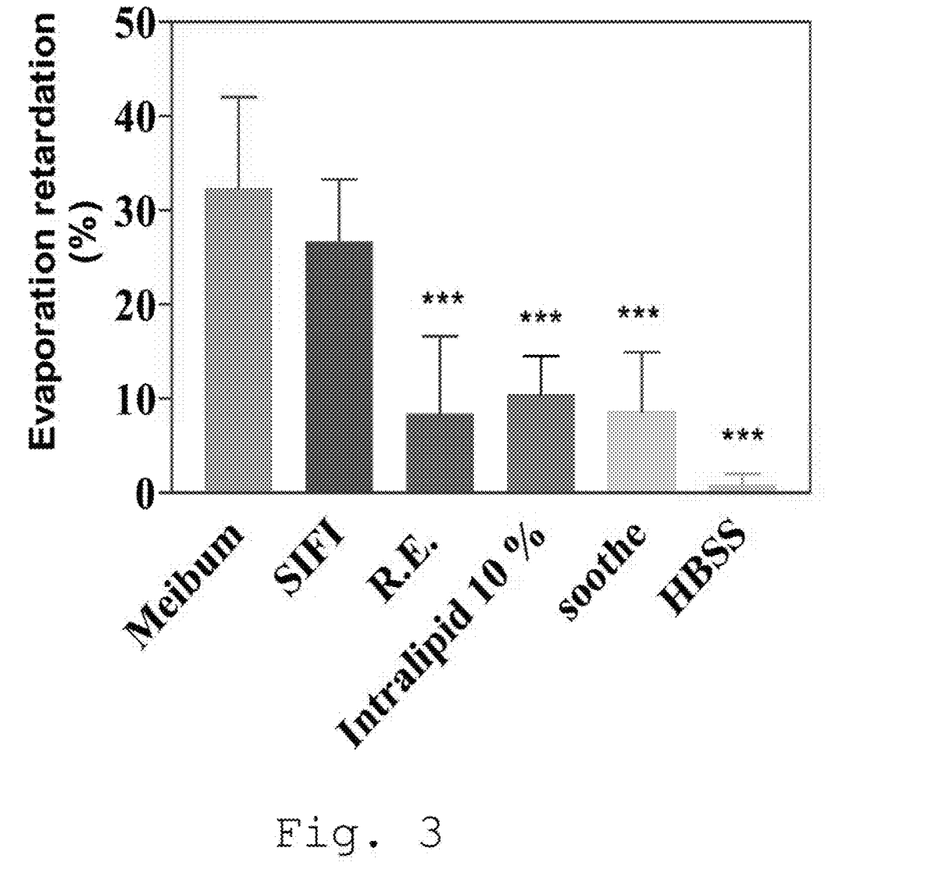
FIG. 3 represents a graph in which the delay percentages of the evaporation of the tear's aqueous layer are compared between the product of the invention, the Meibomian gland and several commercial products.

It was observed, as reported in the table of FIG. 2, that unlike the mineral oils, in the animal and vegetal oils of natural origin, ester triglycerides of fatty acids with long chains containing one or more double bonds are frequent, mainly: linoleic acid C18:2, oleic acid C18:1, palmitoleic acid C16:1, linolenic C18:3 and fatty acids of the Omega-3 series such as eicosapentaenoic acid C20:5 n3, docosenoic acid C22:6. Such oils further stabilise the composition, object of the invention.

In particular, it is known that the fatty acids (EFA) of the Omega-3 series (such as alpha-linolenic acid (ALA), eicosapentaenoic acid (EPA) and docosenoic acid (BHA)) and Omega-6 series (such as linoleic acid (LA) and arachidonic acid (AA)) is recognised as a modulator action in the inflammatory and immune processes.

It was moreover observed that compositions comprising the abovementioned triglycerides and phospholipids in the described percentages advantageously permit obtaining a more homogenous distribution of the lipid component on the ocular surface, avoiding the formation of oily drops, and thus a dimming of the vision, due to a non-homogenous cover of the ocular surface.

As reported above, the ratio between triglycerides and phospholipids is in the range of 4:1-1:1, preferably is it 3:1, still more preferably 2.3:1.

It was moreover surprisingly found that the addition of a buffer with low ionic force to the compositions advantageously permits maintaining a pH compatible with the physiological pH of the tears in a stable manner at room temperature for a long period of time (shelf life), without interfering with the chemical-physical properties and with the tolerability of the product itself.

Preferably, the buffer can be chosen from among the group composed of Tris, NaOH, histidine, tricine, lysine, glycine, serine adjusted to the correct pH with an acidic component with low ionic force.

In particular, during the various phases which have led to the development of the compositions in emulsion, among the formulations developed the best from the stability standpoint were those buffered with Tris and those with histidine.

Figure 1A:
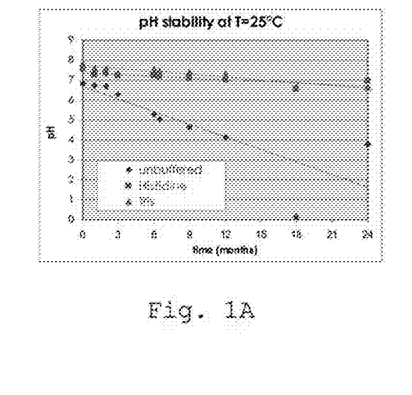
FIG. 1A represents a graph related to comparison of the pH course in three formulations of the invention during the shelf-life at 25° C.
Figure 1B:
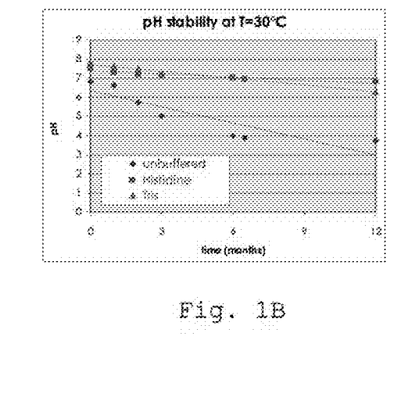
FIG. 1B represents a graph related to the comparison of the pH course in three formulations of the invention during the shelf-life at 30° C.
Figure 1C:
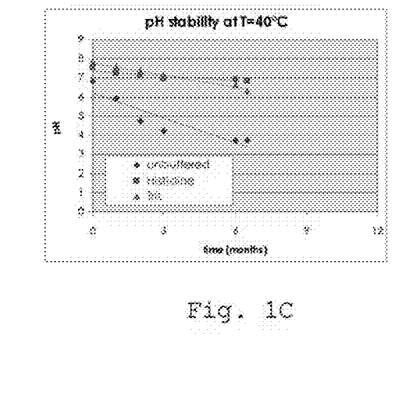
FIG. 1C represents a graph related to the comparison of the pH course in three formulations of the invention during the shelf-life at 40° C.

To test the performances of such formulations with respect to a non-buffered formulation, an experimental test was executed based on the measurement of the pH during the stability study (non-buffered formulation, buffered with histidine or with Tris). As shown in FIGS. 1A-1C, the results obtained show a sudden lowering of pH over time for the non-buffered emulsion, with the formation of free fatty acids at room temperature, while in the emulsions buffered with histidine or with Tris the pH is more stable both at room temperature (25° C.) and at higher temperatures (30 and 40° C.) for a time not less than 24 months.

The compositions of the invention can moreover comprise a non-ionic or low ionic force regulator agent of the osmotic pressure, so that the osmotic pressure of the finished product is in the range of 0.100-0.320 Osmol/kg. In particular, said regulator agent of the osmotic pressure is selected from among glycerol, sorbitol, mannitol, ethylene glycol, propylene glycol, dextrose. The regulator agent of the osmotic pressure is present in sufficient quantities to obtain an osmotic pressure analogous to that of the tear fluid.

The compositions can also comprise stabilising agents, surfactants, antioxidants and/or anti-microbe preservatives, thickening agents, linear or ramified chain polymers, amino acids such as, for example: tocopherol, free fatty acids and their salts, polysorbate, Pluronic®, Cremophor®, HPMC, hyaluronic acid, xanthan gum, parabens, benzalkonium chloride, polyhexamethylene biguanide (PHMB), arginine, lysine, glycine, etc.

As mentioned above, the compositions of the invention are in the form of oil-water emulsion, which are modified at the moment of contact with the ocular surface, their structure being rearranged. This signifies that the compositions are capable of being distributed on the ocular surface, in particular being integrated with the Meibomian gland, as shown by the in vitro experiments on the evaporative flow reduction of the tear, described below.

It was moreover observed, with in vivo experiments conducted on man, that the lipid film on the ocular surface is formed in a homogenous manner only if the composition contains the previously indicated oils, and preferably for the specific ratios indicated between these and the phospholipids. For example, the presence of medium-chain triglycerides (MCT) or short-chain or mixtures between MCT and long-chain triglycerides, determines a distribution of the lipid part on the non-homogeneous tear film which determines a dimming of the sight and poor ocular tolerability due to the specific length of the carbon chain of the oil.

A process example is described below for the production of the compositions which are object of the invention.

Process for the Preparation of Pharmaceutical Formulations Based on Apolar and Polar Lipids for Ophthalmic Use The process for the preparation of pharmaceutical formulations based on apolar and polar lipids as described above, comprises the following steps:

preparing, at about 70±15° C. in one container, the aqueous phase comprising water and possibly all the water-soluble components described;

separately preparing, at about 70±15° C., the oily phase comprising the phospholipid component and the oily component and possible all the liposoluble components, stirring until a homogenous phase is obtained;

adding the oily phase to the aqueous or vice versa;

bringing it to the desired volume with water;

preparing a rough emulsion by using a turbine;

adjusting the pH to the physiological value with an acidic or basic solution, if necessary;

homogenising and stabilising the emulsion by means of a high pressure homogeniser;

sterilising the emulsion at 120±10° C. for a time necessary to reach the $F_0$ (microbe mortality necessary to ensure the sterility of the product);

cooling the emulsion to 20±10° C.

Preferably, the water-soluble components pursuant to the first step are chosen from among those previously described.

Preferably, the liposoluble components pursuant to the second step are chosen from among those previously described.

In the case of emulsions containing a lipophile active principle, this can be incorporated in the oily step before the addition of the phospholipids.

An amphoteric active principle can instead be incorporated in the complete oily phase (oil+phospholipids).

Amphoteric active principles can be incorporated in the complete composition before sterilisation, if thermostable, or, in asepsis, in the previously sterilised complete formulation.

In accordance with the stabilisation of the claimed compositions, considering that the oily part of the emulsions can become rancid already during the steps of preparation and then stability at room temperature, it was observed that more stable products are obtained if the working operations of the raw materials and the semi-worked product up to the sterilisation of the final product are executed in an atmosphere free of oxygen or with oxygen pressure values of less than 3%. This in fact permits avoiding the oxidation of the double bonds present in the fatty acid chains of natural phospholipids and triglycerides which make up the formulation. A possible oxidation of the product in fact causes formulation instability (becoming rancid, separation of the phases) and formation of toxic molecules (peroxide radicals). Also the packaging of the product must be carried out by protecting the composition of the air, immediately after the sterilisation.

In accordance with a specific embodiment of the aforesaid process, the preparation process, made in an atmosphere free of oxygen or with very low oxygen pressure values, consists of placing two containers under magnetic stirring at controlled temperature) (70°, one with the oily phase containing the phospholipids and all the fatty or liposoluble components in the above-indicated ratios and quantities, the other with the aqueous phase containing water and all the hydrosoluble components. When both phases are homogenous, the oily phase is slowly added to the aqueous phase by using the turboemulsifier or high pressure homogeniser at a speed of 5000 revolutions/min. The mixture stirs for about 15 min, at the end of which it is sterilised, cooled and then packaged.

All of the variants can in any case be carried out with the most suitable conditions deemed by the man skilled in the art.

Preferred but non-limiting examples of compositions according to the invention are reported in the following tables.

TABLE 1

| 10% Unbuffered emulsion | (% w/w) |
|---|---|
| Soy oil | 7.0% |
| Phospholipids of the egg yolk | 3.0% |
| Glycerol | 2.0% |
| Water (as needed) | 100 ml |

TABLE 2

| 5% Unbuffered emulsion | (% w/w) |
|---|---|
| Soy oil | 3.5% |
| Phospholipids of the egg yolk | 1.5% |
| Glycerol | 2.2% |
| Water (as needed) | 100 ml |

TABLE 3

| 1% Unbuffered emulsion | (% w/w) |
|---|---|
| Soy oil | 0.7% |
| Phospholipids of the egg yolk | 0.3% |
| Glycerol | 2.2% |
| Water (as needed) | 100 ml |

TABLE 4

| 10% Emulsion buffered with histidine | (% w/w) |
|---|---|
| Soy oil | 7.0% |
| Phospholipids of the egg yolk | 3.0% |
| Glycerol | 1.7% |
| L-Histidine | 0.4% |
| HCl (as needed) for pH 7.5 | — |
| Water (as needed) | 100 ml |

TABLE 5

| 10% Emulsion buffered with Tris | (% w/w) |
|---|---|
| Soy oil | 7.0% |
| Phospholipids of the egg yolk | 3.0% |
| Glycerol | 1.8% |
| Tris base | 0.242% |
| HCl (as needed) for pH 7.6 | — |
| Water (as needed) | 100 ml |

TABLE 6

| 5% Emulsion buffered with tricine | (% w/w) |
|---|---|
| Fish oil | 3.5% |
| Phospholipids of the egg yolk | 1.5% |
| Glycerol | 2.0% |
| Tricine | 0.32% |

TABLE 6-continued

| 5% Emulsion buffered with tricine | (% w/w) |
|---|---|
| HCl (as needed) for pH 7.6 | — |
| Water (as needed) | 100 ml |

TABLE 7

| 10% Emulsion buffered with glycine | (% w/w) |
|---|---|
| Fish oil | 7.0% |
| Phospholipids of the egg yolk | 3.0% |
| Glycerol | 1.8% |
| Glycine | 0.16% |
| HCl (as needed) for pH 7.6 | — |
| Water (as needed) | 100 ml |

TABLE 8

| 10% Emulsion buffered with NaOH | (% w/w) |
|---|---|
| Soy oil | 7.0% |
| Phospholipids of the egg yolk | 3.0% |
| Glycerol | 1.8% |
| 0.01M NaOH | 0.05% |
| HCl (as needed) for pH 7.6 | — |
| Water (as needed) | 100 ml |

TABLE 9

| 10% Medicated Emulsion buffered with L-histidine | (% w/w) |
|---|---|
| Dexamethasone 21 β-palmitate | 0.16% |
| Soy oil | 7.0% |
| Phospholipids of the egg yolk | 3.0% |
| Glycerol | 1.7% |
| L-histidine | 0.40% |
| HCl (as needed) for pH 7.2 | — |
| Water (as needed) | 100 ml |

TABLE 10

| 10% Medicated emulsion buffered with TRIS | (% w/w) |
|---|---|
| Levocabastine | 0.05% |
| Soy oil | 7.0% |
| Phospholipids of the egg yolk | 3.0% |
| Glycerol | 1.8% |
| TRIS base | 0.24% |
| HCl (as needed) for pH 7.2 | — |
| Water (as needed) | 100 ml |

TABLE 11

| 10% Medicated emulsion buffered with L-histidine | (% w/w) |
|---|---|
| Olopatadine | 0.1% or 0.2% |
| Soy oil | 6.0% |
| Phospholipids of the egg yolk | 4.0% |
| Glycerol | 1.7% |
| L-histidine | 0.60% |
| HCl (as needed) for pH 7.0 | — |
| Water (as needed) | 100 ml |

TABLE 12

| 10% Medicated emulsion buffered with L-histidine | (% w/w) |
| --- | --- |
| Latanoprost | 0.005% |
| Soy oil | 6.0% |
| Phospholipids of the egg yolk | 4.0% |
| Glycerol | 1.7% |
| L-histidine | 0.60% |
| HCl (as needed) for pH 7.0 | — |
| Water (as needed) | 100 ml |

Such examples can also be actuated with different salts of the active principles or with active principles different from those indicated in the examples.

Further, olopatadine and levocabastine can be used also at a concentration between 0.02% and 0.2% alone or in combination with each other or with glucocorticoids, while latanoprost can be used at a concentration ranging between 0.002% and 0.01%. For instance, the glucocorticoids can be selected among Fluocinolone acetonide, Fluticasone propionate, Fludroxycortide, Difluprednate, Flumetasone pivalate, Beclometasone dipropionate, Betamethasone, Budesonide, Alclometasone dipropionate, Clobetasol propionate, Clobetasone butyrate, Desonide, Desoximetasone, Diflorasone diacetate, Fluocinonide, Halometasone, Triamcinolone acetonide, Ulobetasol proprionate, Amcinonide, Clocortolone pivalate, Dexamethasone, Diflucortolone, Fludrocortisone acetate, Fluprednidene acetate, Halcinonide, Mometasone furoate, Prednicarbate, Fluclorolone acetonide, Dichlorisone acetate, Fluocortolone, Methylprednisolone, Hydrocortisone, Fluocortin butyl, their salts and esters and mixture thereof.

Figure 4:
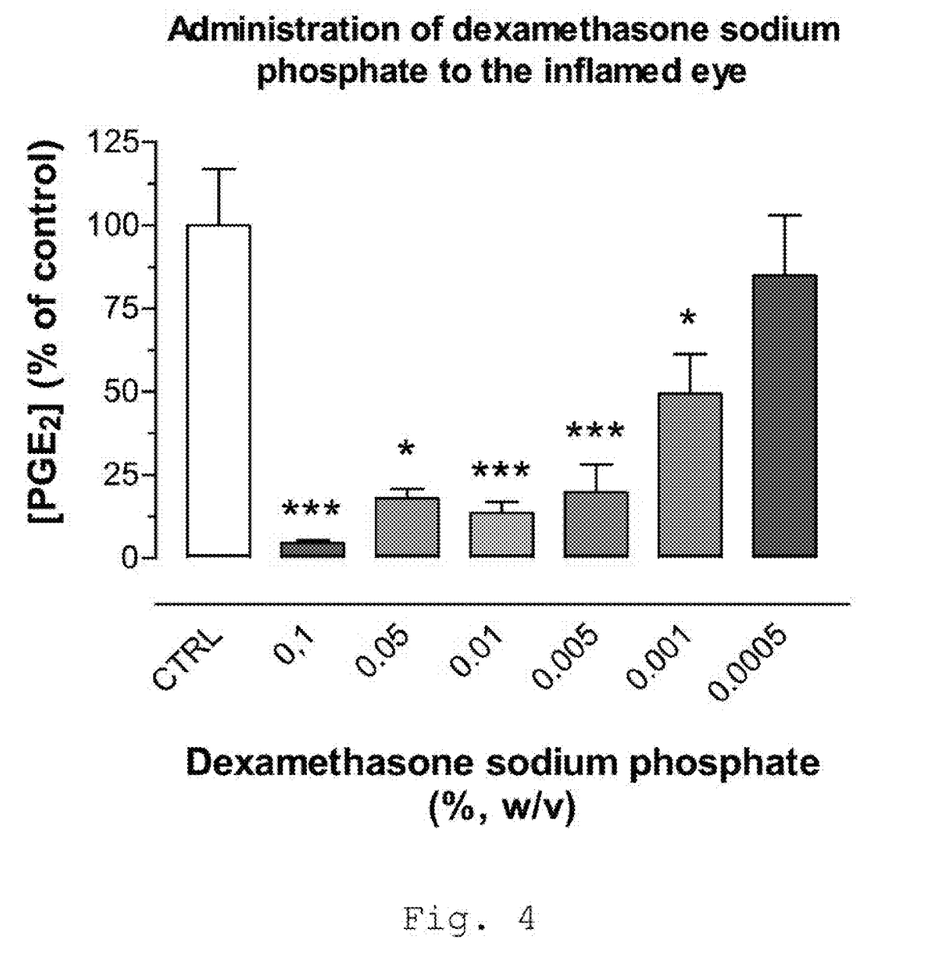
FIG. 4 represents a graph in which the effectiveness of different concentrations of dexamethasone sodium phosphate are compared with regard to the inhibition of PGE2 (prostaglandins E2) accumulation in the aqueous humour of rabbits treated intravitreally with bacterial lipopolysaccharide.

In a model of experimental uveitis in rabbits, we showed that dexamethasone sodium phosphate is able to exert significant anti-inflammatory effects at concentrations as low as 0.001% (FIG. 4).

It is widely accepted that the long-term ophthalmic administration (>2 weeks) of glucocorticoids, at commonly used therapeutic concentrations, is associated with an increased risk of ocular hypertension and opacification of lenses. In fact, the clinical use of ophthalmic glucocorticoids is limited to two weeks therapeutic courses. Notably, the unwanted effects of ophthalmic glucocorticoids are directly linked to the amount of drug delivered to the eyes.

Following this line of reasoning, the use of concentrations in the lower part of the range we have selected (0.001%-1%) may be especially useful in long-term treatment of ocular surface conditions characterised by inflammation such as allergy, dry eye, or treatment following photorefractive keratectomy (PRK) or corneal transplantation.

In conclusion, especially for ocular surface inflammatory pathologies, glucocorticoids used also at concentrations near the lower part of the range we have selected will maintain their efficacy while showing improved ophthalmic safety profile and therefore allow for longer therapeutic courses.

Further active principles can be selected from the group consisting in fluoroquinolones preferably of second, third and fourth generation such as ciprofloxacin, ofloxacin, levofloxacin, trovafloxacin, moxifloxacin, gemifloxacin or mixtures thereof or in their "fixed" combination (formulation containing at least two different actives) with antinflammatories such as glucocorticoids or with other antimicrobials such as macrolides, cephalosporins or betalattamines. Fluoroquinolones concentration can vary between 0.1% and 0.6%.

The following were determined of several compositions, object of the present invention: stability, tolerability, effectiveness in the reduction of the tear film evaporation, capacity of diffusion in the Meibomian gland, antiallergic/antiinflammatory effectiveness.

Stability and Tolerability

All of the compositions reported in the description of the object of the present invention are well tolerated at the ophthalmic level.

The stability of the buffered formulations is at least 24 months at room temperature.

Effectiveness of the Compositions Against Evaporation of the Aqueous Component of the Tear Film It is known to the experts of opthalmology that the lipid layer of the tear, produced by the Meibomian gland, is capable of reducing the surface tension of the tear film and considerably slowing the evaporation speed of the water from the underlying layer.

The emulsions, object of the present invention, demonstrate particular properties with respect to other ophthalmic formulations containing lipids and/or polymers, in particular for the peculiar capacity to lower the surface tension of a balanced saline solution by at least 30 mN/m also following additions on the order of 1% by volume with respect to the drop, in the hanging drop system described below and reported in the work Miano F. et al, J. Phys: Condens. Matter 16 (2004) S2461-S2467.

The compositions which are object of the present invention are moreover surprisingly capable of keeping the evaporation speed of a balanced saline solution low, independent of the temperature conditions, relative humidity, by the presence or lack of a natural lipid layer and by the volumetric proportions between solution and emulsion.

In order to verify the capacity of the compositions which are the object of the present invention to reduce the evaporation flow of the aqueous part of the tear, the evaporation speed was determined of a balanced saline solution (HBSS) in the absence of or in the presence of Meibomian glands, of the emulsions object of the invention or of commercial comparison products.

The model of the hanging drop was used, on an optical contact angle (OCA20, Dataphysics, Germany) connected to two Hamilton syringes with electronic metering and a chamber with controlled temperature and relative humidity (RH), inside which the drop is dispensed.

The evaporation speed was calculated as the difference of the drop dimensions in a given time interval (15 seconds), by means of processing of the images provided by a CCD camera. The monitoring of the evaporation speed was repeated 80 times for a total of 20 minutes in each experiment.

The experimental data was expressed as a reduction of the evaporation speed with respect to the balanced saline solution by means of the following formulas:

$$J_w = K * \frac{(100 - R.H.)}{100}$$

in which $J_W$ is the evaporation flow expressed in $g^{*m-2}*s^{-1}$, R.H. is the relative humidity and K is a constant dependent on the temperature.

The ratio between the evaporation flow $J_m$ in the presence of Meibomian glands or Meibomian glands+ophthalmic composition (composition object of the invention or commercial comparison products) with respect to $J_w$ (evaporation flow of the solution, expressed in $g^{*m-2}*s^-$) is defined as:

$$\phi = 1 - (J_m/J_w)$$

where $\phi$, of a value in the range of 0-1, represents the resistance to evaporation determined by a homogenous distribution of the lipids at the interface with the aqueous layer. The data was processed with the DATAPHYSICS software [Miano F. et al, J. Phys: Condens. Matter 16 (2004) S2461-S2467]. The following described experiments determine the evaporation speed of aqueous solutions with reference to the evaporation phenomena of the tears in patients affected by evaporative dry eye. Together with the evaporation speed, the surface tension of the fluid is detected which is an important property of the tear fluid. The data presented regards the effect of several preparations for ophthalmic use on the evaporation speed of a model system representative of the tear film.

After having dispensed a drop of HBSS (Hank's Balanced Salt Solution, containing $CaCl_2.H_2O$, 0.19 mg/mL; $MgSO_4$, 0.098 mg/mL; KCl, 0.40 mg/mL; $H_2PO_4$, 0.06 mg/mL; $NaHCO_3$, 0.35 mg/mL; NaCl, 8.0 mg/ml and D-glucose 1.0 mg/mL) of the 12 µl volume, one skillfully adds a known volume, for example 1 µl, of natural lipid solution in chloroform and waits 2 minutes for the chloroform evaporation and the simultaneous formation of a lipid layer at the liquid-air interface. A known volume is then added of ophthalmic solution under examination in the range of 10%-50% by volume of the volume of the drop. The formulations reported in the following table 13 were tested.

TABLE 13

| Tested Formulations | Composition |
| --- | --- |
| 10% Non-buffered emulsion | Non-buffered emulsion containing 7% soy seed oil; 3% lecithin; 2.2% glycerol in purified water. |
| 10% Emulsion buffered with histidine | Emulsion containing 7% soy seed oil; 3% lecithin; 2.2% glycerol in purified water buffered with histidine. |
| 10% Emulsion buffered with TRIS | Emulsion containing 7% soy seed oil; 3% lecithin; 1.8% glycerol in purified water buffered with TRIS. |
| Refresh Endura (USA) | Commercial product containing 1% glycerol, 1% polysorbate 80, carbomer, mannitol, ricin oil, sodium hydroxide in water |
| TSP (Tamarind Seed Polysaccharide) | Polysaccharides extracted from the tamarind seed (0.5% or 1.0%); mannitol, benzalkonium chloride in water |

Example 1

The evaporation speed is measured of the balanced saline solution (HBSS) and of the ophthalmic compositions, in different conditions of temperature and relative humidity.
Conditions: T=25±1° C.; R.H.=66% controlled by means of a saturated solution of $NaNO_2$.

TABLE 14

| Composition | Jw |
| --- | --- |
| HBSS | $8.26 \times 10-5 \pm 3.1 \times 10-6$ g/m²/s |
| HBSS + Meibomian Glands | $4.46 \times 10-5 \pm 1.67 \times 10-6$ g/m²/s |
| 10% Emulsion | $6.37 \times 10-5 \pm 2.54 \times 10-6$ g/m²/s |

Conditions: T=36±1° C. R.H.=15% controlled by means of LiCl saturated solution.

TABLE 15

| Composition | Jw |
| --- | --- |
| HBSS | $3.919 \times 10-4 \pm 4.1 \times 10-5$ g/m²/s |
| HBSS + Meibomian Glands | $2.555 \times 10-4 \pm 5.4 \times 10-5$ g/m²/s |
| 10% Emulsion | $2.802 \times 10-4 \pm 4.01 \times 10-5$ g/m²/s |

This example demonstrates how the compositions which are object of the invention are capable of reducing the evaporation speed of the aqueous solution in a similar manner to the Meibomian glands, in different environmental conditions, and in particular when the relative humidity is low, as often occurs in offices, airports, in airplanes, cars, etc.

Example 2

The evaporation speed of the balanced saline solution (HBSS) is measured, in comparison with the solution with Meibomian glands, in different temperature and relative humidity conditions and with the addition of different composition volumes under study or for comparison.
Conditions: T=36±1° C.; R.H.=15%.
One adds 1 µl/10 µl of composition under study or for comparison.

TABLE 16

| | Meibomian Glands | Refresh Endura | 1% TSP | 10% Emulsion |
| --- | --- | --- | --- | --- |
| Φ | 0.337 ± 0.086 | 0.341 ± 0.050 | 0.032 ± 0.061 | 0.322 ± 0.097 |

Conditions: T=36±1° C.; R.H.=15%.
One adds 5 µl/10 µl of composition under study or for comparison.
The ratio between ophthalmic preparation and fluid is more similar to the drops of an eyewash in the eye than the addition of only one µl.

TABLE 17

| | Meibomian Glands | Refresh Endura | 1% TSP | 10% Emulsion |
| --- | --- | --- | --- | --- |
| Φ | 0.337 ± 0.086 | 0.041 ± 0.077 | 0.120 ± 0.048 | 0.325 ± 0.080 |

The optimal value of Φ is that given by the Meibomian glands. The closer the Φ of the tested compounds approaches this value, the more effective these compounds will be in the physiological reduction of the evaporation of the aqueous part of the tear film. From this example, it can be inferred how Refresh Endura, effective for additions of low volumes to the drop, if added in volumes close to those of the drops of a eyewash undoes the lipid film, while TSP never reaches a physiological Φ value. The emulsions, on the other hand, show a physiological effectiveness in reducing the evaporation of the aqueous solution, in all used experimental conditions.

Example 3

The surface tension is measured of the balanced saline solution (HBSS), of the saline solution in the presence of Meibomian lipids and of the ophthalmic solutions and emulsions described above.
Conditions: T=25° C.; U.R.=95% for a solution saturated with disodium sulphate dodecahydrate.

TABLE 18

| Composition | $(10^{-3}$N/m) | NOTES |
| --- | --- | --- |
| HBSS Saline solution | 72.38 ± 0.27 | |
| HBSS saline solution with Meibomian glands | 48.60 ± 1.25 | 0.05 µl* in 15 µl of HBSS |
| 10% histidine-buffered emulsion | 55.11 ± 0.29 | |

TABLE 18-continued

| Composition | ($10^{-3}$N/m) | NOTES |
|---|---|---|
| 10% histidine-buffered emulsion in saline HBSS | 26.64 ± 0.45 | 0.1 µl in 10 µl of HBSS |
| 10% histidine-buffered emulsion in saline HBSS | 39.66 ± 0.21 | 3 µl in 12 µl of HBSS |
| Refresh Endura | 39.72 ± 0.28 | |
| Refresh Endura in saline HBSS | 42.15 ± 0.45 | 0.1 µl in 10 µl of HBSS |
| 0.5% TSP | 47.39 ± 0.60 | |
| 1.0% TSP | 47.71 ± 0.66 | |
| 0.5% TSP in saline HBSS | 66.78 ± 0.48 | 1 l in 15 l of HBSS |

*solution at 0.4%.

The experiment demonstrates the surprising properties of the emulsions of the invention for lowering the surface tension when they are in contact with a saline solution containing bivalent cations ($Ca_2$+; $Mg_2$+).

It is clear from the experiment that the simple presence of a normal surface active agent (Refresh Endura or TSP formulation) does not determine a lowering of the effective surface tension, as instead occurs for the emulsions which are the object of the invention.

The data obtained for Refresh Endura or TSP indicates that when these are inserted in a similar system to the natural system, they do not succeed in being well distributed in the Meibomian lipids.

The reduction values of the surface tension obtained for the emulsions which are object of the invention and the proportionality with the volumes added to the aqueous solution indicate, on the other hand, that such compositions are well integrated with the Meibomian lipids.

Example 4

In order to evaluate the capacity of the compositions, object of the present invention, to integrate and reproduce the function of the Meibomian gland lipids, the reduction was evaluated of the evaporation speed determined by different compositions currently available on the national and international market compared with the compositions of the invention and with the natural Meibomian gland lipids. The hanging drop system was also used in this case. The indicated compositions were compared in the below-reported table 19.

TABLE 19

| 10% Emulsion (SIFI) | Egg yolk lecithin, Soy oil in TRIS buffer |
|---|---|
| Refresh endura* RE (USA) | Ricin oil, polysorbate-80, Carbomer 1342 and glycerine |
| 10% Intralipid** | Soy oil, lecithin, glycerine |
| Soothe* | 4.5% Mineral oil (Restoryl), polisorbate-80 |

*ophthalmic composition
**intravenous nutrient composition

Figure 5:
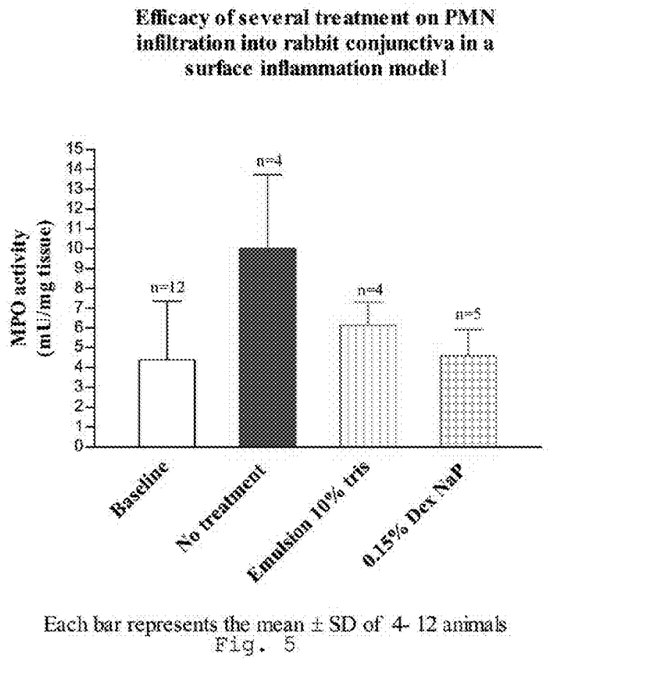
FIG. 5 represents a graph in which the effectiveness of the different treatments is compared with regard to the infiltration of PMN in the rabbit conjunctiva in a surface inflammation model.

As can be observed from the graph reported in FIG. 5, unlike the other tested compositions, the lipid emulsion which is object of the invention (SIFI) reduces the evaporation, in our in vitro model, in a statistically significant manner and similar to the Meibomian lipids (respectively 28% and 31%), while the products which can be found on the market are less effective statistically.

It was also observed, with rheological measurements, that the natural Meibomian lipid film has mainly elastic behaviour in the presence of the surface compression originated from the eyelid during blinking, which favours the reconstruction of the tear film after blinking.

It was found that the compositions, object of the invention, significantly correspond to the physical properties which characterise the diffusion of the natural Meibomian lipid film at the air/water interface.

Such characteristic fluidity is advantageous for the correct reconstruction of the tear film after blinking. This was not an obvious result, since it was found that other compositions containing phospholipids and some commercial emulsions produce a substantially different interface.

The compositions in SIFI emulsion demonstrate possessing the physical properties which characterise the diffusion of the natural Meibomian lipid film at the air/water interface.

This particular feature renders the compositions of the invention particularly suited for carrying drugs for ophthalmic use which require rapid diffusion, integration and compatibility with the tear fluid, determining a good distribution and kinetics in the ocular tissues and synergising the effects of several drugs.

After administration in the conjunctival sac, in fact, due to the ions present in the tear, the phases composing the emulsion are separated, releasing the active principle.

In particular, when the qualitative-quantitative composition of the lipid layer is altered, as in the case of subjects affected by ocular dryness, dry eye syndrome by evaporation, allergies, bacterial or viral infections etc. . . . the compositions of the present invention are capable of being integrated with the deficient lipid layer, restoring its physiological conditions.

Antiallergic and Anti-Inflammatory Effectiveness

Figure 6:
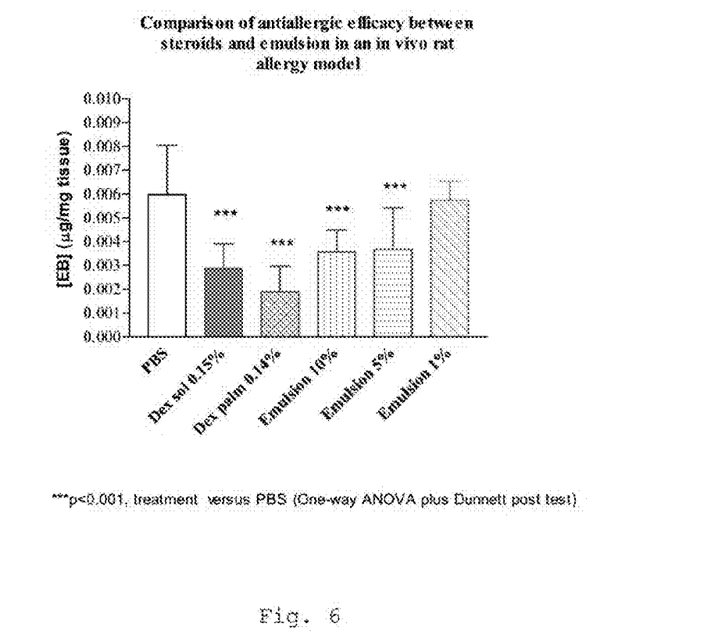
FIG. 6 represents a graph in which the comparison is shown in terms of anti-allergic effectiveness between glucocorticoids and emulsions in an in vivo allergy model in rats.

As mentioned in the introductive part of the present description, several compositions which are object of the present invention demonstrate surprising antiallergic and antiinflammatory properties. It was also observed that by administering the composition of the invention comprising antiinflammatory or antiallergic drugs one obtains considerably and unexpectedly improved therapeutic responses with respect to the use of said drugs formulated in known compositions. In one experiment conducted on glucocorticoids with an in vivo surface inflammation model, the compositions of the invention have unexpectedly demonstrated effectiveness comparable with that of glucocorticoids. (FIG. 6).

Such effect was then investigated in an in vivo immunological allergy model, in particular of active ocular anaphylaxis in the rat. The rat ocular tissue, in fact, responds to systemic anaphylaxis phenomena. The experimental model used possesses characteristics similar to that observed in human pathologies, whose clinical signs are: dilation of the blood capillaries, conjunctival oedema and increased vascular permeability (Bloch J K, Ohman J, Waltin J, and Cygan R N. "Potentiated reagin response: Initiation with minute doses of antigen and alum followed by infection with *Nippostrongylus brasiliensis*" J Immunol 110:197, 1973).

20 Wistar male rats were used of about 150-175 g weight. The animals were immunised by means of an intraperitoneal injection with 100 mg of ovalbumin plus 20 mg of alum in 1 ml of sterile 0.9% NaCl. After 14 days, the animals were divided into groups and received the topical challenge with the antigen (10 ml of 100 mg/ml ovalbumin in PBS). Immediately before the challenge, the Evans Blue (EB) colorant (1.25 mg/100 g/1 ml of PBS) was injected in the caudal vein of the animals previously anesthetised with ethers.

Following the breakout of the ocular anaphylactic reaction, the mediators of the allergy (histamine, serotonin, leukotrienes, platelets activating factor-PAF, eosinophil chemotactic factor etc.), which determine the above-described clinical signs, are released by mastocytes and basophils.

In particular, the histamine released by the activated mastocytes and basophils, causes an increase in the vascular permeability, with consequent extravasation of the Evans Blue-albumin by the blood circulation and accumulation in the ocular tissues, causing edema (Baird R S, Bloch J K, and Allansmith M R. "Edema test for assessing ocular anaphylaxis". Curr Eye Res 2: 657, 1983).

The vascular permeability being an adequate parameter for evaluating the intensity of the allergic response, the extravasation of the colorant in the ocular tissues, measured 30 minutes after the induction of the anaphylaxis, was used as a marker in the allergic reaction.

These compositions were tested:

---
control: water and 2.2% glycerol
10% emulsion
5% emulsion
1% emulsion
0.15% Dexamethasone sodium phosphate solution
0.14% Dexamethasone palmitate in 10% emulsion
---

The substances were topically applied (15 µl) in the right eye of the animals, while the left eye was not treated.

The emulsions were administered 5, 4, 3, 2, 1 hours before the ocular challenge, according to the protocol reported in literature for the corticoglucocorticoids (Calonge M C, Pastor J C, Herreras J M and Gonzales J L. "Pharmacologic modulation of vascular permeability in ocular allergy in the rat". Invest Opthalmol V is Sci 28: 264, 1987).

After the challenge, the animals developed the allergic reaction at conjunctival level, already visible after the first 5 minutes with conjunctival and palpebral edema, with a maximum of 30 minutes.

Thirty minutes after the challenge, the animals were sacrificed by cervical dislocation. The eyes and the lids were removed, weighed and immersed in an extraction solution consisting of acetone and 0.5% sodium sulphate respectively in 14:6 ratio and held at room temperature under stirring. Twenty-four hours later, the samples were centrifuged at 2000 rpm for 10 minutes and the intensity of the colour of the supernatant was read at the spectrophotometer at 620 nm.

For every experiment, standard reference curves were prepared for transforming the absorbance unit in mg/ml of solution, then the data was normalised per mg of tissue. The data was expressed as EB extravasation percentage in the ocular tissues of the treated animals with respect to the control animals, not pharmacologically treated.

Figure 7:
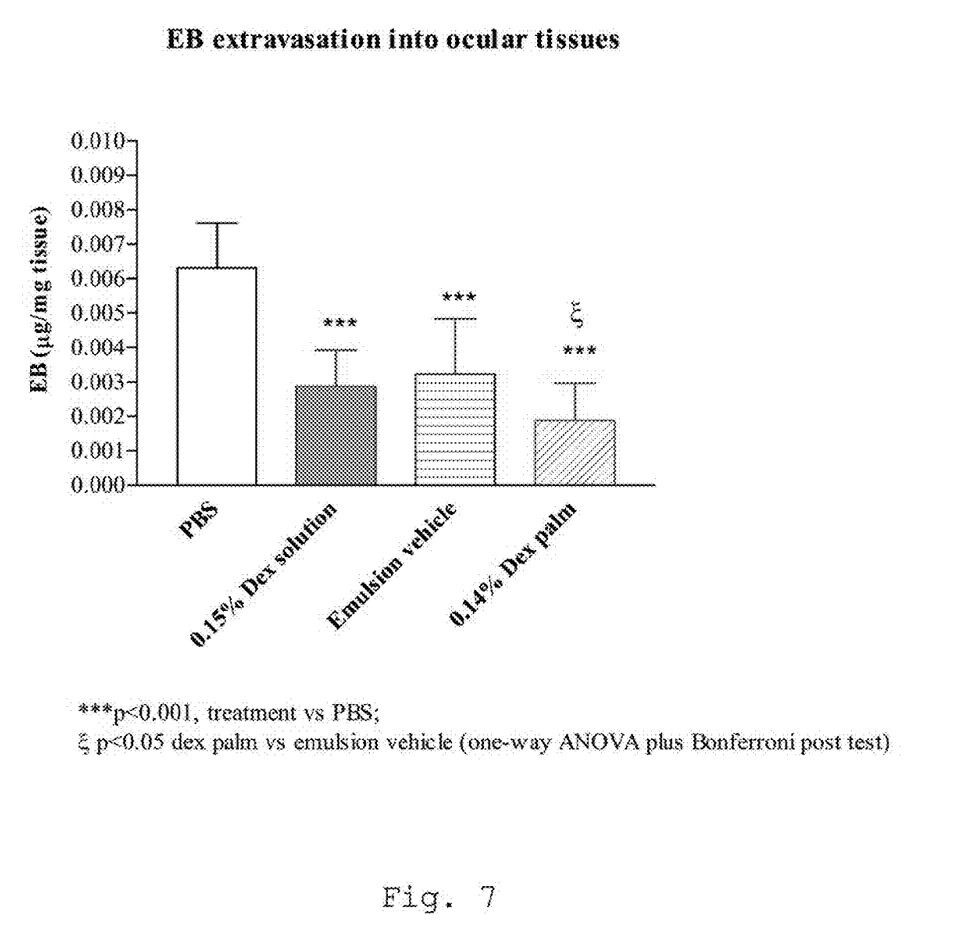
FIG. 7 represents a comparison graph in the EB (Evans Blu) extravasation in the ocular tissues between glucocorticoids and vehicle of the invention.

As is known in FIG. 7, in the utilised model a dose-dependent effectiveness was observed in the tested compositions, which assumes statistical significance for the emulsions containing concentrations of the oily component greater than 1%.

In particular, it was observed that the 10% emulsion shows a 50% inhibition of the extravasation of colorant with respect to the control and the 5% emulsion exerts approximately a 37% inhibition of the allergic reaction. It is also observed from the experiment that the emulsion in which the dexamethasone palmitate is carried has a synergistic effect on the action of the active principle which, although at 0.14%, has a greater effect than the solution of 0.15% dexamethasone sodium phosphate.

In particular, moreover, the synergistic action of the emulsion on the effect of the dexamethasone palmitate gives rise, if compared with the effectiveness of its vehicle (10% emulsion), to a greater statistical significance than that obtained by comparing 0.15% solution and PBS (FIG. 8).

As can be appreciated from that described above, the present patent application makes available a pharmaceutical composition for ophthalmic use which permits employing natural substances.

Moreover, the man skilled in the art can make numerous variants to the composition, all moreover coming within the protective scope of the claims herein enclosed.

The invention claimed is:

1. A pharmaceutical composition for ophthalmic use, said composition comprising
   a phospholipid component composed of zwitterionic egg yolk phospholipids and
   an oily component consisting of one or more oils of essentially natural origin, and free of any synthetic oil or mineral oil, wherein
   the weight ratio of the oily component to the phospholipid component is in the range of 4:1 to 1:1,
   the phospholipid component is present from 0.1%-5% by weight, and
   the oily component is present from 0.3%-15% by weight, and
   a buffer with low ionic force in an amount sufficient to maintain the pH of the finished product in the range of 6.5-8, said buffer being selected from the group consisting of histidine and Tris and combinations thereof, to maintain stability of the composition.

2. A pharmaceutical composition according to claim 1, wherein the ratio between the oily component and phospholipid component is about 3:1.

3. A pharmaceutical composition according to claim 1, wherein the phospholipid component comprises phosphatidylcholine in quantities from 50-70%, phosphatidylethanolamine from 5-20%, sphingomyelin from 1-10%, lysophosphatidylcholine from 1-10%, neutral lipids from 2%-15% with respect to the total weight of the phospholipids.

4. A pharmaceutical composition according to claim 1, wherein the oily component is selected from the group consisting of soy oil, olive oil, sunflower oil, fish oil, borage oil, sesame oil, hemp oil, corn oil, cotton oil and mixtures thereof.

5. A pharmaceutical composition according to claim 1, wherein the oily component comprises oils in the form of apolar triglycerides.

6. A pharmaceutical composition according to claim 5, wherein the fatty acids which compose the apolar triglycerides are selected from the group consisting of myristic acid, linoleic acid, oleic acid, linolenic acid, palmitic acid, palmitoleic acid, stearic acid, eicosapentaenoic acid, arachidonic acid, docosenoic acid and mixtures thereof.

7. A pharmaceutical composition according to claim 1, further comprising a non-ionic or low ionic force regulator agent for maintaining the osmotic pressure of the composition in the range of 0.100-0.320 Osmol/kg.

8. A pharmaceutical composition according to claim 7, wherein said regulator agent of the osmotic pressure is selected from the group consisting of glycerol, sorbitol, mannitol, ethylene glycol, propylene glycol, dextrose and mixtures thereof.

9. A pharmaceutical composition according to claim 1, further comprising at least one additional agent selected from the group consisting of stabilisers, surfactants, cosurfactants, antioxidants and/or anti-microbe preservatives, thickeners, linear or ramified chain polymers, amino acids and mixtures thereof.

10. A pharmaceutical composition according to claim 9, wherein said additional agent is selected from the group consisting of tocopherol, free fatty acids and their salts or derivatives, polysorbate, pluronic, cremophor, HPMC, hyaluronic acid, xanthan rubber, parabens, benzalkonium chloride, polyhexamethylene biguanide (PHMB), arginine, lysine, glycine, alcohols and mixtures thereof.

11. A pharmaceutical composition according to claim 1, further comprising an active principle or a fixed combination of active principles.

12. Pharmaceutical composition according to claim 11, wherein said active principles are selected from the group consisting of olopatadine, levocabastine, latanoprost, glucocorticoids, fluoroquinolones of second, third or fourth generation and mixtures thereof.

13. Pharmaceutical composition according to claim 12, wherein said active principles are in fixed combination with betalattamines, cephalosporines and macrolides.

14. Pharmaceutical composition according to claim 12, wherein said olopatadine and levocabastine are used at a concentration between 0.02% and 0.2%, said latanoprost is used at a concentration between 0.002% and 0.01%, said glucocorticoids are used at a concentration between 0.001% and 1% and said fluoroquinolones of second, third or fourth generation are used at a concentration between 0.1% and 0.6%.

15. A pharmaceutical composition for ophthalmic use according to claim 1, said composition consisting essentially of:

| | |
|---|---|
| Soy oil | 7.0 wt. % |
| Phospholipids of egg yolk | 3.0 wt. % |
| Glycerol | 2.0 wt. % |
| Water (as needed) | (balance). |

16. A pharmaceutical composition for ophthalmic use according to claim 1, said composition consisting essentially of:

| | |
|---|---|
| Soy oil | 3.5 wt. % |
| Phospholipids of egg yolk | 1.5 wt. % |
| Glycerol | 2.2 wt. % |
| Water (as needed) | (balance). |

17. A pharmaceutical composition for ophthalmic use according to claim 1, said composition consisting essentially of:

| | |
|---|---|
| Soy oil | 0.7 wt. % |
| Phospholipids of egg yolk | 0.3 wt. % |
| Glycerol | 2.2 wt. % |
| Water (as needed) | (balance). |

18. A pharmaceutical composition for ophthalmic use according to claim 1, said composition consisting essentially of:

| | |
|---|---|
| Soy oil | 7.0 wt. % |
| Phospholipids of egg yolk | 3.0 wt. % |
| Glycerol | 1.7 wt. % |
| L-histidine | 0.4 wt. % |
| HCl (as needed) for pH 7.5 | — |
| Water (as needed) | (balance). |

19. A pharmaceutical composition for ophthalmic use according to claim 1, said composition consisting essentially of:

| | |
|---|---|
| Soy oil | 7.0 wt. % |
| Phospholipids of egg yolk | 3.0 wt. % |
| Glycerol | 1.8 wt. % |
| Tris base | 0.242 wt. % |
| HCl (as needed) for pH 7.6 | — |
| Water (as needed) | (balance). |

20. A pharmaceutical composition for ophthalmic use according to claim 1, said composition consisting essentially of:

| | |
|---|---|
| Fish oil | 3.5 wt. % |
| Phospholipids of egg yolk | 1.5 wt. % |
| Glycerol | 2.0 wt. % |
| Tricine | 0.32 wt. % |
| HCl (as needed) for pH 7.6 | — |
| Water (as needed) | (balance). |

21. A pharmaceutical composition for ophthalmic use according to claim 1, said composition consisting essentially of:

| | |
|---|---|
| Fish oil | 7.0 wt. % |
| Phospholipids of egg yolk | 3.0 wt. % |
| Glycerol | 1.8 wt. % |
| Glycine | 0.16 wt. % |
| HCl (as needed) for pH 7.6 | — |
| Water (as needed) | (balance). |

22. A pharmaceutical composition for ophthalmic use according to claim 1, said composition consisting essentially of:

| | |
|---|---|
| Soy oil | 7.0 wt. % |
| Phospholipids of egg yolk | 3.0 wt. % |
| Glycerol | 1.8 wt. % |
| 0.01M NaOH | 0.05 wt. % |
| HCl (as needed) for pH 7.6 | — |
| Water (as needed) | (balance). |

23. A pharmaceutical composition for ophthalmic use according to claim 1, said composition consisting essentially of:

| | |
|---|---|
| Dexamethasone 21 β-palmitate | 0.16 wt. % |
| Soy oil | 7.0 wt. % |
| Phospholipids of egg yolk | 3.0 wt. % |
| Glycerol | 1.7 wt. % |
| L-histidine | 0.40 wt. % |
| HCl (as needed) for pH 7.2 | — |
| Water (as needed) | (balance). |

24. A pharmaceutical composition for ophthalmic use according to claim 1, said composition consisting essentially of:

| | |
|---|---|
| Levocabastine | 0.05 wt. % |
| Soy oil | 7.0 wt. % |
| Phospholipids of egg yolk | 3.0 wt. % |
| Glycerol | 1.8 wt. % |
| TRIS base | 0.24 wt. % |
| HCl (as needed) for pH 7.2 | — |
| Water (as needed) | (balance) |

25. A pharmaceutical composition for ophthalmic use according to claim 1, said composition consisting essentially of:

| | |
|---|---|
| Olopatadine | 0.1 or 0.2 wt. % |
| Soy oil | 6.0 wt. % |
| Phospholipids of egg yolk | 4.0 wt. % |
| Glycerol | 1.7 wt. % |
| L-histidine | 0.60 wt. % |
| HCl (as needed) for pH 7.0 | — |
| Water (as needed) | (balance). |

26. A pharmaceutical composition for ophthalmic use according to claim 1, said composition consisting essentially of:

| | |
|---|---|
| Latanoprost | 0.005 wt. % |
| Soy oil | 6.0 wt. % |
| Phospholipids of egg yolk | 4.0 wt. % |
| Glycerol | 1.7 wt. % |
| L-histidine | 0.60 wt. % |
| HCl (as needed) for pH 7.0 | — |
| Water (as needed) | (balance). |

27. A pharmaceutical composition according to claim 11, wherein the active principle consists of any one of salts or esters of said active principles.

28. A medication comprising the pharmaceutical composition according to claim 1.

* * * * *